United States Patent [19]

Lori et al.

[11] Patent Number: 6,046,175
[45] Date of Patent: *Apr. 4, 2000

[54] PROCEDURE TO BLOCK THE REPLICATION OF REVERSE TRANSCRIPTASE DEPENDENT VIRUSES BY THE USE OF INHIBITORS OF DEOXYNUCLEOTIDES SYNTHESIS

[75] Inventors: Franco Lori, Parma, Italy; Andrea Cara; Wen-Yi Gao, both of Rockville, Md.; Robert C. Gallo, Bethesda, Md.

[73] Assignee: The United States of America as represented by the Department of Health and Human Services, Washington, D.C.

[*] Notice: This patent is subject to a terminal disclaimer.

[21] Appl. No.: 08/245,259

[22] Filed: May 17, 1994

Related U.S. Application Data

[63] Continuation-in-part of application No. 08/065,814, May 21, 1993, abandoned.

[51] Int. Cl.$^7$ ..................................................... A61K 31/70
[52] U.S. Cl. ............................. 514/45; 514/579; 514/588; 536/27.14; 536/28.2; 536/27.8; 560/313
[58] Field of Search ................................. 435/235.1, 236, 435/238, 240.1, 240.2; 514/45, 46, 49, 50, 579, 588; 536/27.14, 28.2, 27.8; 560/313

[56] References Cited

U.S. PATENT DOCUMENTS

| | | | |
|---|---|---|---|
| 4,708,818 | 11/1987 | Montagnier et al. | 435/5 |
| 5,026,687 | 6/1991 | Yarchoan et al. | 514/45 |
| 5,110,600 | 5/1992 | Green | 424/450 |
| 5,300,059 | 4/1994 | Rubinstein et al. | 604/408 |
| 5,521,161 | 5/1996 | Malley, I et al. | 514/45 |
| 5,736,526 | 4/1998 | Malley, II et al. | 514/45 |
| 5,736,527 | 4/1998 | Malley, III et al | 514/45 |

FOREIGN PATENT DOCUMENTS

| | | |
|---|---|---|
| 0206497 | 12/1986 | European Pat. Off. . |
| 8701284 | 3/1987 | WIPO . |
| WO 92/08699 | 5/1992 | WIPO . |
| WO 93/12782 | 7/1993 | WIPO . |
| WO 93/23368 | 11/1993 | WIPO . |
| WO 94/27590 | 12/1994 | WIPO . |
| WO 95/17899 | 7/1995 | WIPO . |

OTHER PUBLICATIONS

Villani et al., "Pharmacokinetics of Hydroxyurea in Patients Infected with Human Immunodeficiency Virus Type I," *Journal of Clinical Pharmacology*, 36, 117–121 (1996).

Gao et al., "Low Levels of Deoxynucleotides in Peripheral Blood Lymphocytes: A Strategy to Inhibit Human Immunodeficiency Virus Type 1 Replication," *Proc. Nat. Acad. Sci. USA*, 90, 8925–8928 (Oct. 1993).

*Biochemicals/Organic Compounds for Research and Diagnostic Reagents*, Sigma Chemical Co. (catalog), St. Louis, MO, 1992, pp. 321, 341–342.

Feorino et al., "Prevention of Activation of HIV–1 by Antiviral Agents in OM–10.1 Cells," *Antiviral Chemistry & Chemotherapy*, 4(1), 55–63 (1993).

Snyder et al. (I), "Effects of Hydroxyurea and Thymidine Derivatives on the Uptake and Metabolism of Deoxycytidine and Arabinosylcytosine in Log Phase and Contact–Inhibited Human Fibroblasts," *Molecular Pharmacology*, 28(6), 574–580 (1985); see p. 578 in particular.

Licastro et al., "Inhibition of Polymerases–α and –β Completely Blocks DNA Repair Induced by UV Irradiation in Cultured Mouse Neuronal Cells," *Biochem. Biophys. Res. Comm.*, 132(3), 929–933 (Nov. 15, 1985).

Busso et al., "Cellular Pharmacology and Anti–HIV Activity of 2',3'–Dideoxyguanosine," *AIDS Res. Human Retroviruses*, 6(9), 1139–1146 (1990).

R. S. Root–Bernstein(I), "AIDS Is More Than HIV: Part I," *Genetic Engineering News*, Sep. 1, 1992, pp. 4–6.

R. S. Root–Bernstein(II), "AIDS Is More Than HIV: Part II," *Genetic Engineering News*, Sep. 15, 1992, pp. 4–5.

"Kaposi's Sarcoma and Pneumocystis Pneumonia Among Homosexual Men," *Morbidity Mortality Weekly Rept.*, vol. 30(25), Centers for Disease Control, Jul. 3, 1981, pp. 305–308.

Barre–Sinoussi et al., "Isolation of a T–Lymphotropic Retrovirus from a Patient at Risk for Acquired Immune Deficiency Syndrome (AIDS)," *Science*, 220, 868–871 (1983).

Fauci (I), "The Human Immunodeficiency Virus: Infectivity and Mechanisms of Pathogenesis," *Science*, 239, 617–622 (Feb. 1988).

Fauci (II), "Multifactoral Nature of Human Immunodeficiency Virus Disease: Implications for Therapy," *Science*, 262, 1011–1018 (Nov. 12, 1993).

Zack et al., "HIV–1 Entry into Quiescent Primary Lymphocytes: Molecular Analysis Reveals a Labile, Latent Viral Structure," *Cell*, 61, 213–222 (Apr. 20, 1990).

Bukrinsky et al., "Quiescent T Lymphocytes as an Inducible Virus Reservoir in HIV–1 Infection," *Science*, 254, 233–237 (Oct. 18, 1991).

Schnittman et al., "The Reservoir for HIV–1 in Human Peripheral Blood Is a T Cell that Maintains Expression of CD4," *Science*, 245, 305–308 (Jul., 1989).

(List continued on next page.)

*Primary Examiner*—Cecilia Tsang
*Assistant Examiner*—L. Eric Crane
*Attorney, Agent, or Firm*—Knobbe, Martens, Olson & Bear, LLP

[57] ABSTRACT

A method for inhibiting replication of reverse transcriptase dependent virus in plant or animal cells, comprising the step of administering to said cells a compound that depletes the intracellular pool of deoxyribonucleoside phosphate in an amount effective to inhibit replication of said virus. Hydroxyurea is one such suitable compound. Also disclosed is a method for producing incomplete reverse-transcriptase dependent viral DNA, by administering a deoxyribonucleoside phosphate-depleting drug to cells infected with such a virus.

22 Claims, 6 Drawing Sheets

OTHER PUBLICATIONS

Fox et al., "Lymphoid Germinal Centers Are Resevoirs of Human Immunodeficiency Virus Type 1 RNA," *J. Infectious Diseases*, 164, 1051–1057 (Dec., 1991).

Hirsch et al., "Therapy for Human Immunodeficiency Virus Infection," *N. Engl. J. Medicine*, 328(23), 1686–1695 (Jun. 10, 1993).

Pauwels et al., "Rapid and Automated Tetrazolium–Based Colorimetric Assay for the Detection of Anti–HIV Compounds," *J. Virological Methods*, 20, 309–321 (1988).

Yarchoan et al., "Clinical Pharmacology of 3'–Azido–2', 3'–dideoxythymidine (Zidovudine) and Related Dideoxynucleosides," *N. Engl. J. Medicine*, 321(11), 726–738 (Sep. 14, 1989).

Chow et al., "Use of Evolutionary Limitations of HIV–1 Multidrug Resistance to Optimize Therapy," *Nature*, 361, 650–654 (1993).

Lori et al., "Hydroxyureas an Inhibitor of Human Immunodeficiency Virus–Type 1 Replication," *Science*, 266, 801–805 (Nov. 4, 1994).

Karlsson et al., "Hydroxyurea Increases the Phosphorylation of 3'–fluorothymidine and 3'–Azidothymidine in CEM Cells," *Eur. J. Biochem.*, 186, 689–694 (1989).

Marquez et al., "Acid–Stable 2'–Fluoro Purine Dideoxynucleosides as Active Agents Against HIV," *J. Med. Chem.*, 33(3), 978–985 (1990).

Snyder et al. (II), "The Accumulation of DNA Breaks Due to Incision; Comparative Studies with Various Inhibitors," Ch. 2 in DNA Repair and Its Inhibition, Nucleic Acids Symposium Series No. 13, Collins et al. eds., IRL Press, Oxford, England, 1984, pp. 13–33.

Vila et al., "Absence of Viral Rebound After Treatment of HIV–Infected Patients with Didanosine [ddI] and Hydroxycarbamide [aka Hydroxyurea]," *Lancet*, 350(9078), 635–636 (Aug. 30, 1997).

Schoofs, "The Berlin Patient," *The New York Times Magazine*, pp. 32–35, Jun. 21, 1998.

Altman, L.K., New York Times, p. 38, Sunday, Sep. 17, 1995, "Study Challenges AZT Role as the Chief Drug for H.I.V.".

Biron et al., *Journal of Acquired Immune Deficiency Syntromes and Human Retrovirology*, 10(1):36–40, 1995, "Anti– HIV Activity of the Combination of Didanosine and Hydroxyurea in HIV–1–Infected Indivuduals".

Fischl, *AIDS Clin. Rev.*, 94:167–187, 1993, "Treatment of HIV Disease in 1993/1994".

Gao, *Aids Research and Human Viruses*, 10(1): Supp. 3, Abstract No. 355, 1994, (Sep. 1994). "Mechanisms of the Enhanced Anti–HIV–1 Activites of 2', 3'–Dideoxynucleoside Analogs by Hydroxyurea".

Gao et al., *Mol. Pharmacol.*, 46(4): 767–772, 1994, (Oct. 1994). "Anti–Human Immunodeficiency Virus Type 1 Activity of Hydroxyurea in Combination with 2', 3'–Dideoxynucleosides".

Goulaiouic et al., *C.R. Acad. Sci. Paris*, 317: 430–436, 1994. "Potentiation of 2', 3'–Dideoxycytidine (ddc) by Hydroxyurea and Thymidine on the Moloney Murine Leukemia Virus (MoMLV) Early Replicative Steps".

Goulaouic et al., *Virology*, 200: 87–97, 1994. "Exogenous Nucleosides Promote the Completionof MoMLV DNA Synthesis on GO–Arrested Balb c/3t3 Fibroblasts".

Hao et al., *Molecular Pharmacolocy*, 34:431–435, 1988, "Factors Determining the Activity of 2', 3'–Dideoxynucleosides in Supressing Human Immunodeficiency Virus In Vitro".

Langreth, The Wall Street Journal, p. B12, Nov. 21, 1995, "FDA Gives Approval to Glaxo, Sequus to Market Separate AIDS Therapies".

Lien, *Progress in Drug Research*, 31: 101–126, 1987, "Ribonucleotide reductase inhibitors as anticancer and antiviral agents".

Lori et al., *International Conference on Aids*, 10(1): 8, Abstract No. 007b, 1994 (Aug. 7–12, 1994). "Hydroxyurea as a Novel Potent Inhibitor of HI–1 Replication".

Malley et al., *The Lancet*, 343(8908): 1292, 1994, (May 21, 1994). "Suppression of HIV Production in Resting Lymphocytes by Combining Didanosine and Hydroxamate Compounds".

Malley, *Proc. Nat. Acad. Sci. USA*, 91(23): 11017–11021, Nov. 1994, "Synergistic Anti–Human Immunodeficiency Virus Type 1 Effect of Hydroxamate Compounds with 2', 3'–Dideoxyinosine in Infected Resting Human Lymphocytes".

Meyerhans et al., *Journal of Virology*, 68(1): 535–540, 1994, (Jan. 1994). "Restriction and Enhancement of Human Immunodeficiency Virus Type 1 Replication by Modulation of Intracellular Deoxynucleosides Triphosphate Pools".

New York Times, p. B19, Nov. 24, 1995, "Study Puts Risk of H.I.V. in Young U.S. Men at 1 in 92".

Vila et al., *Lancet*, 348(9021): 203–204, Jul. 20, 1996, "1–year follow–up of the use of hydroxycarbamide and didanosine in HIV Infection".

Medina, D.J. et al., "Ganciclovir Antagonizes the Anti–Human Immunodeficiency Virus Type I Activity of Zidovudine and Didanosine In Vitro", Antimicrobial Agents and Chemotherapy, vol. 36, No. 5, pp. 1127–1130, May 1992.

Simonelli, C. et al.; "Hydroxyurea as an Antiviral Drug in HIV Infected Patients: Clinical, Immunological and Virological Evaluation", Presented at: The Fifth European Conference on Clinical Aspects and Treatement of HIV Infection, Copenhagen, Denmark, Sep. 26–29, 1995, Abstract No. 84.

Meyerhans, Andreas, et al.; VIII International Conference on AIDS/III STD World Congress; Amsterdam, The Netherlands; Jul. 19–24, 1992; vol. 2; Poster Abstracts; "The Intracellular Nucleotide Pool Effects HIV Replication"; p A22.

T'ang, Anne, et al.; J. Med. Chem. 1985, 28, 1103–1106; "Optimization of the Schiff Bases of n–Hydroxy–N'–aminoguanidine as Anticancer and Antiviral Agents".

Sharma, Satyavan, et al.; Progress in Drug Research; vol. 31, 1987, pp. 101–126; "Ribonucleotide reductase inhibitors as anticancer and antiviral agents".

Gao, Wen–Yi, et al.; Mol. Pharmacology, 46:767–772 (1994), "Anti–Human Immunodeficiency Virus Type 1 Activity of Hydroxyurea in Combination with 2', 3'–Dideoxynucleosides".

Lori, et al.; Antiviral Res. (1994), vol. 23, Suppl.d. p. 63; "Hydroxyurea Inhibits HIV–1 Replicatin by Inducing Low dNTP Levels. A Cellular Enzyme as a Target to Inhibit HIV–1".

Matsumoto, Steven S., et al.; The Journal of Immunology; vol. 131, No. 6, Dec. 1983; pp. 2762–2766; "Inhibition of RNA Synthesis by Deoxyadenosine Plus Deoxycoformycin in Resting Lymphocytes".

Wilson, James M., et al.; J. Clin. Invest, vol. 64, Nov. 1979, 1475–1484; "Purinogenic Immunodeficiency Diseases: Differential Effects of Deoxyadenosine and Deoxyguanosine on DNA Synthesis in Human T Lymphoblasts".

Albert, Daniel A., et al.; Experimental Cell Research 179 (1988) 417–428; "Deoxyadenosine Toxicity and Cell Cycle Arrest in Hydroxyurea–Resistant S49 T–Lymphoma Cells".

Perno, Carlo–Federico, et al.; The Journal of Experimental Medicine; vol. 168; Sep 1988; pp. 1111–1125; "Inhibition of Human Immunodeficiency Virus Replication in Fresh and Cultured Human Peripheral Blood Monocytes/Macrophages by Azidothymidine . . . ".

Gao, Wen–Yi, et al.; Clinical Research; 42:280A; 1994; "Anti–HIV–1 Activity Of Hydroxyurea In Combination With 2',3'–Dideoxynucleosides".

Coffin, H. "Retroviridae and Their Replication" *Fundamental Virology*, 2nd Edition, (Fields, et al. eds., Raven Press, Ltd., New York 1991), pp. 545–708.

Huber, et al. "Human Immunodeficiency Virus I Reverse Transcriptase" J. of Biological Chem. 264(8): 4669–4678 (1989).

Hubscher, H. "DNA Polymerases in Prokaryotes and Eukaryotes: Mode of Action and Biological Implications" Experientia 39(1): 1–25 (1983).

Ji, et al. "Analysis of Mutagenesis Induced by a Thermolabile T4 Phage Deoxycytidylate Hydroxymethylase Suggests Localized Deoxyribonucleotide Pool Imbalance" Mol. Gen. Genet. 226: 257–264 (1991).

Kati, et al. "Mechanism and Fidelity of HIV Reverse Transcriptase" J. of Biol. Chem. 267(36): 25988–25997 (1992).

Lori, et al. "Viral DNA Carried by Human Immunodeficiency Virus Type 1 Virions" J. of Virol. 66(8):5067–5074 (1992).

McCune, et al. "Endoproteolytic Cleavage of gp160 Is Required for the Activation of Human Immunodeficiency Virus" Cell 53: 55–67 (1988).

Pegoraro, et al. "Thymidine Kinase, Deoxycytidine Kinase and Deoxyctidylate Deaminase Activities in Phytohaemagglutinin Stimulated Human Lymphocytes" Experimental Cell Res. 68: 283–290 (1971).

Popovic, et al. "Detection, Isolation, and Continuous Production of Cytopathic Retroviruses (HTLV–III) from Patients with AIDS and Pre–Aids" Science 224: 497–500 (1984).

Robinson, W. "Hepadnaviridae and Their Replication" *Fundamental Virology,* 2nd Edition, (Fields, et al. eds., Raven Press, Ltd., New York 1991), pp. 989–1021.

Stevenson, et al. "HIV–1 Replication is Controlled at the Level of T Cell Activation and Proviral Integration" The EMBO Journal 9(5): 1551–1560 (1990).

Trono, D. "Partial Reverse Transcripts in Virions from Human Immunodeficiency and Murine Leukemia Viruses" J. of Virol. 66(8): 4893–4900 (1992).

Varmus, et al. "Replication of Retroviruses" *Cold Springs Harbor Laboratories* pp. 369–512 (1984).

Derwent Abstract of WO93–23368, Nov. 25, 1993.

Derwent Abstract of WO92–08699, May 29, 1992.

Malley, et al.; The Lancet, vol. 343, May 21, 1994; p. 1292; "Suppression of HIV Production in resting lymphocytes by combining didanosine and hydroxamate compounds".

Goulaouic, et al.; Virology 200, 87–97 (1994); "Exogenous Nucelosides Promote the Completion of MoMLV DNA Synthesis in GO–Arrested Babl c/3T3 Fibroblasts".

Goulaiouic, et al.; C.R. Acad Sci. Paris, Sciences de la vie/Life Sciences, 1994; 317: 430–6; "Potentiation of 2', 3'–dideoxycytidine (ddC) by hydroxyurea and thymidine on the Moloney murine leukemia virus (MoMLV) early replicative steps".

Meyerhans, et al.; Journal of Virology, Jan 1994; pp. 535–540; vol. 68, No. 1; "Restriction and Enhancement of Human Immunodeficiency Virus Type 1 Replication by Modulation of Intracellular Deoxynucleoside Triphosphate Pools".

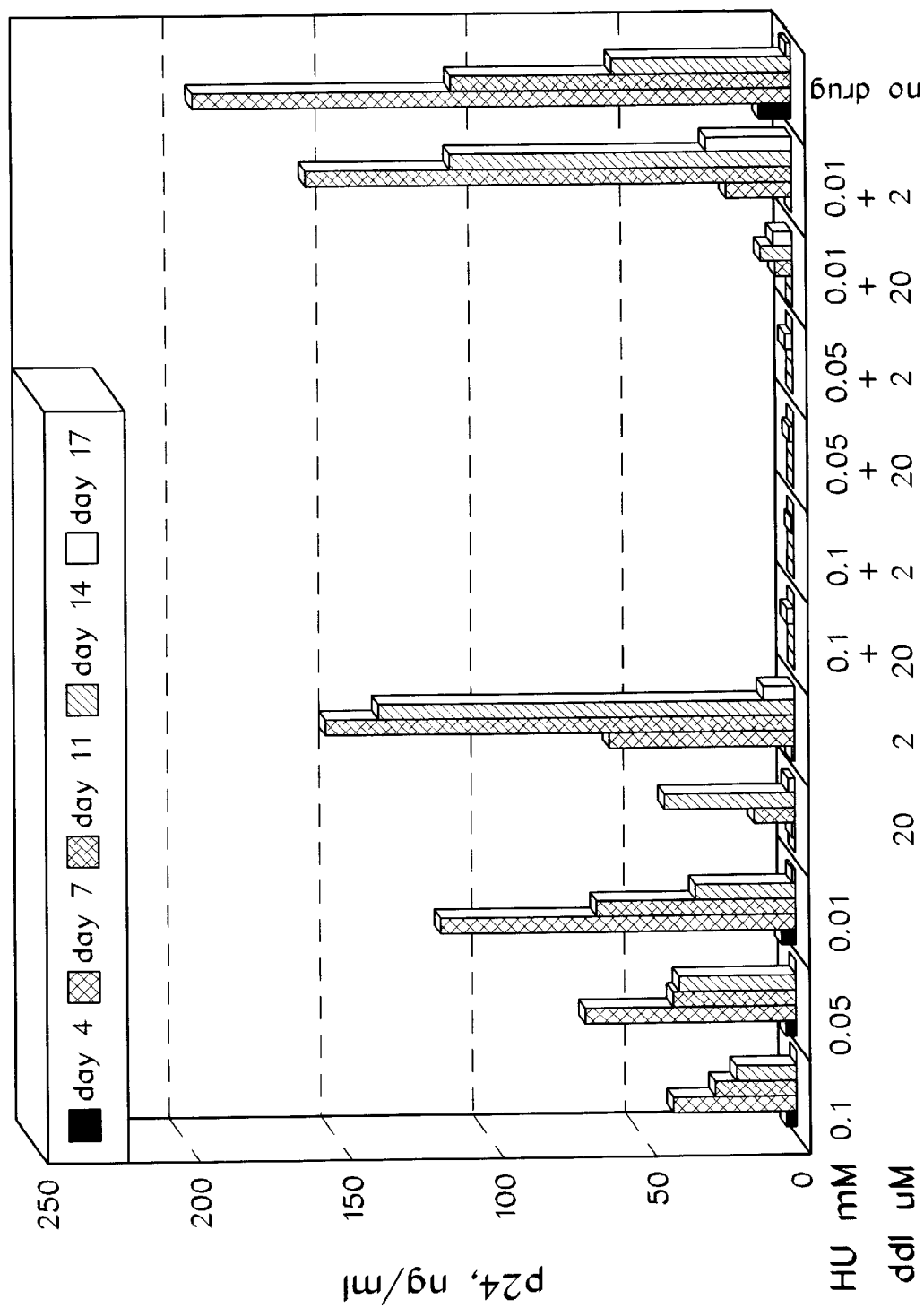

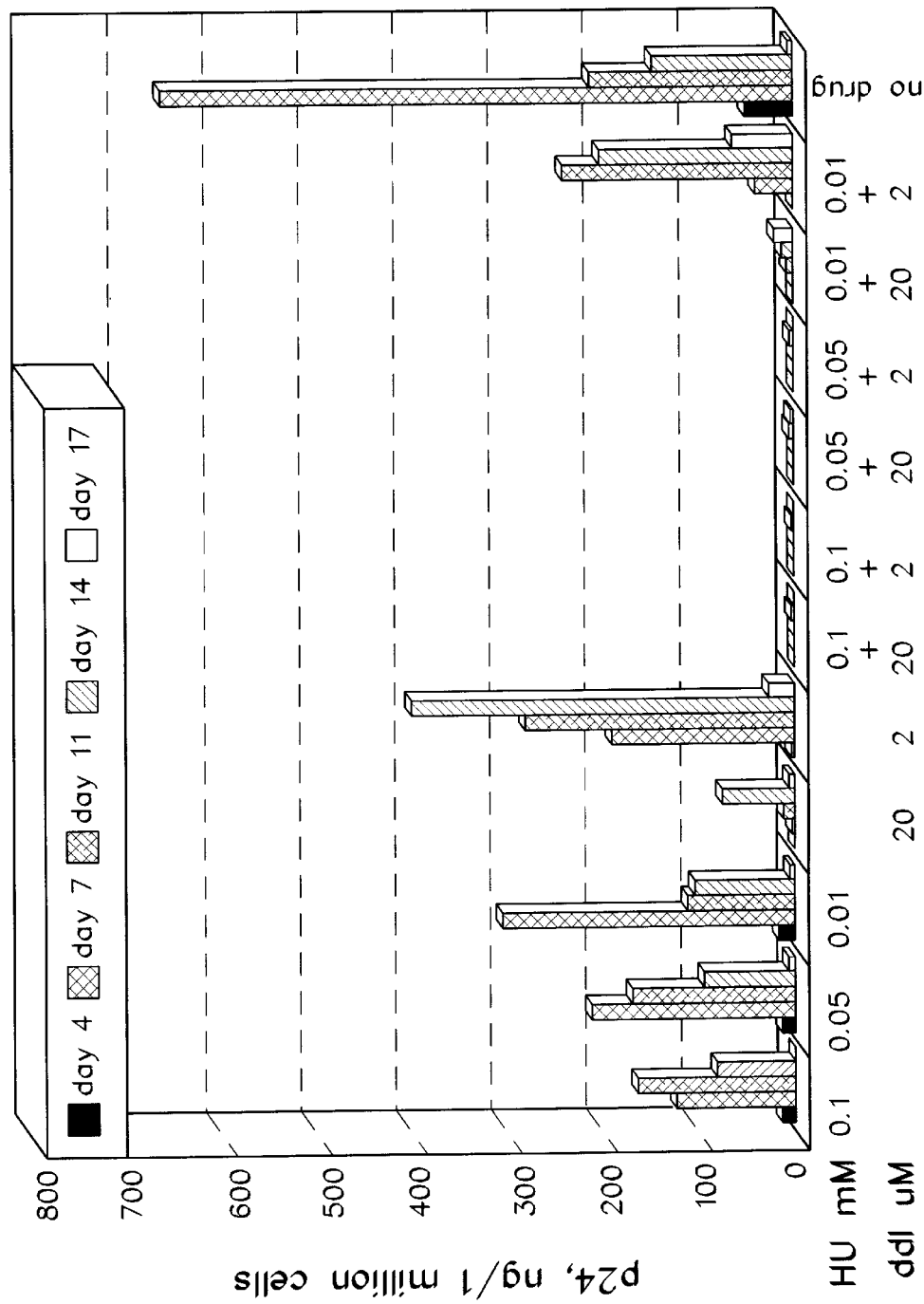

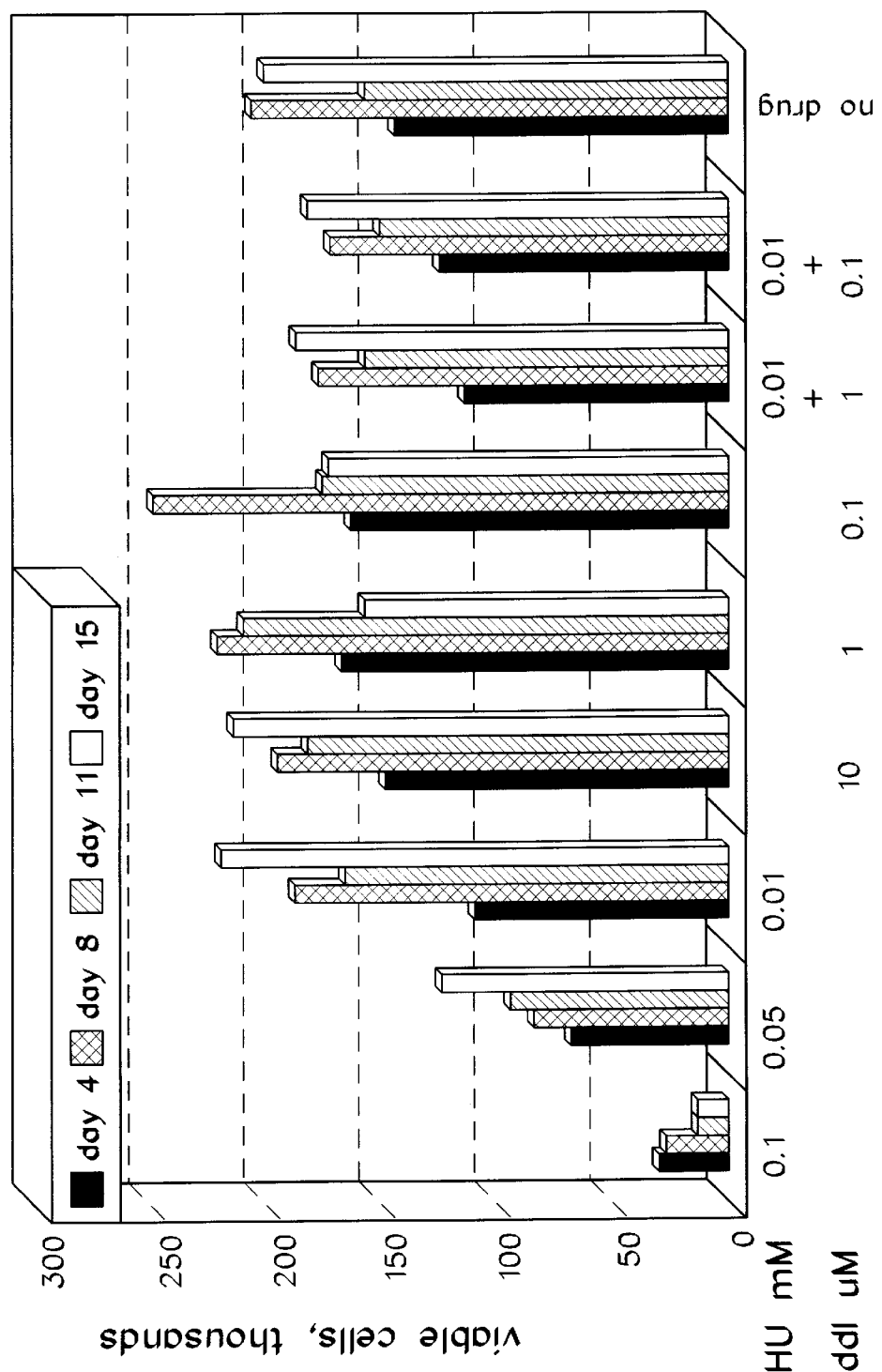

PROCEDURE TO BLOCK THE REPLICATION OF REVERSE TRANSCRIPTASE DEPENDENT VIRUSES BY THE USE OF INHIBITORS OF DEOXYNUCLEOTIDES SYNTHESIS

CROSS-REFERENCE TO RELATED APPLICATION

This application is a continuation-in-part of U.S. application Ser. No. 08/065,814, filed May 21, 1993, now abandoned.

FIELD OF THE INVENTION

The present invention relates generally to the field of reverse transcriptase dependent viruses. More specifically, the invention relates to the use of agents which reduce intracellular concentrations of deoxyribonucleosides as a means to inhibit the replication of reverse transcriptase dependent viruses.

BACKGROUND OF THE INVENTION

Viruses are microorganisms that depend, to some degree, on host cell components for their growth and replication. Viral infection and replication in host cells generally results in disease, whether the host is an animal or plant. Human diseases caused by viral infections include the acquired immunodeficiency syndrome (AIDS) and hepatitis. A general discussion of this field is presented in *Fundamental Virology, Second Edition*, (ed. B. N. Fields, D. M. Knipe, R. M. Chanock, M. S. Hirsh, J. L. Melnick, T. P. Monath, and B. Roizman, Raven Press, Ltd., New York, N.Y. 1991).

Retrovirus Replication

Retroviruses comprise a large family of viruses that primarily infect vertebrates. Many diseases, including the induction of some tumors, are associated with retroviral infection (see *Fundamental Virology*, supra, pp. 645–708). All retroviruses, regardless of their clinical manifestations, have related structures and modes of replication.

Retroviruses contain an RNA genome that is replicated through a DNA intermediate. Inside the cell, the viral genome serves as a template for the synthesis of a double-stranded deoxyribonucleic acid (DNA) molecule that subsequently integrates into the genome of the host cell. This integration occasionally results in the induction of a tumor in the infected host organism. Following integration, a complex sequence of events leads to the production of progeny virions which are released from the infected cell.

Early in the retroviral life cycle, the RNA genome is copied into DNA by the virally encoded reverse transcriptase (RT). This enzyme can use both RNA and DNA templates, thereby producing the first strand of DNA (the negative strand) from the infecting RNA genome and a complementary second strand (the positive strand) of DNA using the first DNA strand as a template. To synthesize these DNA strands, the RT utilizes cellular substrates called deoxynucleoside triphosphates (dNTP).

Human retroviruses can be grouped into the leukemia viruses (HTLV type viruses) and the immunodeficiency viruses (HIV type viruses). HTLV infection may lead to one form of leukemia. Acquired immunodeficiency syndrome (AIDS) is caused by a form of HIV, with HIV-1 being more virulent than HIV-2. Both HTLV and HIV infect peripheral blood lymphocytes (PBL).

Other animal retroviruses include feline leukemia virus (FeLV) and lentiviruses. Virulent FeLV infection generally results in fatal aplastic anemia in cats. Lentiviruses cause a variety of neurological and immunological diseases such as visna in sheep and infectious anemia in horses.

HIV Infection

HIV-1 was first identified as the causative agent of AIDS in 1983. The AIDS pandemic is now one of the most serious health problems worldwide. Catastrophic medical and social consequences are likely to extend into the next century. The World Health Organization (WHO) has estimated that between eight and ten million people are currently infected with HIV, and that approximately ten times as many individuals will be affected in the next decade. The large pool of HIV carriers makes the development of effective antiviral treatments a medical priority.

Hepatitis B Infection

Hepatitis B virus (HBV) is one of at least three (A, B and C) viruses that selectively infect liver cells (for a general discussion of HBV see *Fundamental Virology*, supra, pp. 989–1021). HBV infections tend to be persistent with minimal liver damage or with chronic hepatitis that may lead to cirrhosis or liver cancer (hepatocellular carcinoma or HCC). Worldwide, more than 200 million people infected with HBV.

Other Viruses

Several other viruses that infect humans, animals and plants also depend on reverse transcriptase for replication. These include retroviruses such as the leukemia viruses known to exist in several species, including HTLV-1 in humans, as well as reverse transcriptase dependent DNA viruses, such as the cauliflower mosaic virus (a plant virus).

Antiviral Therapies

There is a critical need to develop effective drug treatments to combat RT dependent viruses such as HIV. Such efforts were recently urged in the United Kingdom-Irish-French Concorde Trial conclusions which reported that the nucleoside analog zidovudine (AZT), a mainstay in the treatment of patients infected with HIV-1, failed to improve the survival or disease progression in asymptomatic patients. Other nucleoside analogs like didanosine (ddI) are currently under evaluation. The effects of ddI on disease progression and patient survival endpoints have not been adequately investigated. Non-competitive HIV-1 RT inhibitors and HIV-1 protease inhibitors have also been recently developed. Despite the high efficacy of these compounds, the initial in vitrolin vivo testing has been characterized by the rapid onset of variants of HIV-1 resistant to these drugs (escape mutants). Despite having different antiviral activities and pharmacokinetics properties, the drugs mentioned here all directly target HIV-1 proteins.

Although this latter approach must be continued, we have developed a different antiviral strategy that targets one or more cellular components that are required for the replication of reverse transcriptase dependent viruses.

SUMMARY OF THE INVENTION

The present invention is based on the discovery that drugs which reduce the intracellular concentration of deoxynucleoside phosphates inhibit the replication of reverse transcriptase dependent viruses. Such drugs act either by inhibiting the intracellular synthesis of deoxynucleoside phosphates or by depleting the intracellular pool of deoxynucleoside phosphates. Viruses sensitive to growth inhibition by limiting deoxynucleoside phosphates are retroviruses, including HIV which causes AIDS, hepatitis B virus, cauliflower mosaic virus, and other reverse transcriptase dependent viruses. As one example, hydroxyurea limits synthesis of the intracellular deoxynucleoside phosphates by inhibiting enzymatic activity of ribonucleoside reductase. Other compounds are known that similarly inhibit accumulation of intracellular deoxynucleoside phosphates by this mechanism or by affecting other biosynthetic steps that lead to production of intracellular deoxynucleoside phosphates. Compounds that limit intracellular deoxynucleoside phosphates can be used in conjunction with antiviral nucleoside phosphate analogs, which are themselves therapeutic as competitive inhibitors of native nucleosides, to increase the effectiveness of antiviral treatment. Compounds that deplete intracellular deoxynucleoside phosphates may be used as an alternative to treatment with antiviral nucleoside phosphate analogs, especially when a virus has become refractory to nucleoside analog treatment.

One aspect of the present invention is a method for inhibiting replication of reverse transcriptase dependent virus in animal cells, comprising the step of administering to the cells a compound that depletes the intracellular pool of deoxyribonucleoside phosphate in an amount effective to inhibit replication of the virus. The virus can, for example, be a retrovirus, or a reverse transcriptase-dependent DNA virus. The deoxynucleoside phosphate depleting compound in one embodiment is a deoxynucleotide synthesis inhibitor. In another embodiment, the deoxynucleoside phosphate depleting compound is an inhibitor of ribonucleotide reductase. One preferred compound is hydroxyurea.

The invention can be used on cells in vitro or in vivo. In various preferred embodiments, the animal is a mammal or a bird. Preferably, the animal is a human.

In one specific embodiment, the virus is the human immunodeficiency virus (HIV), such as HIV-1 or HIV-2, and the cells are human cells. In another specific embodiment, the virus is hepatitis B and the cells are human cells.

The method of the present invention may be practiced by depleting the intracellular pool of deoxynucleoside phosphates to limit viral replication by limiting the rate of DNA chain elongation. For example, AZT and dideoxynucleosides, such as ddI, ddC and 2'-fluoro dideoxynucleosides, so limit viral replication. This can result in premature termination of viral DNA synthesis to produce incomplete viral DNA.

Another aspect of the present invention is a method for inhibiting replication of reverse transcriptase dependent virus in animal cells, comprising the steps of administering to the cells a compound that depletes the intracellular pool of deoxyribonucleoside phosphate, and coadministering to the cells antiviral nucleoside phosphate analogs which compete with the pool of deoxyribonucleoside phosphates. Preferred antiviral nucleoside phosphate analogs include AZT, ddI, and ddC.

A different aspect of the invention relates to a method of producing incomplete viral DNA from reverse transcriptase dependent virus in animal cells, comprising the step of administering to the cells a compound that depletes the intracellular pool of deoxyribonucleoside phosphate in an amount effective to inhibit replication of the virus.

Finally, the invention includes a method for inhibiting replication of reverse transcriptase dependent virus in plant cells, comprising the step of administering to the cells a compound that depletes the intracellular pool of deoxyribonucleoside phosphate in an amount effective to inhibit replication of the virus.

BRIEF DESCRIPTION OF THE FIGURES

FIG. 1a graphically depicts p24 expression in HIV-1 infected PBL as a function of the hydroxyurea and ddI concentrations.

FIG. 1c shows HIV-1 p24 expression normalized to the number of viable cells as a function of the Hu and ddI concentrations.

FIG. 3b graphically depicts the number of viable cells isolated from an HIV-1 infected patient that survived in culture with treatment by hydroxyurea and/or ddI.

DETAILED DESCRIPTION OF THE INVENTION

Figure 1B:
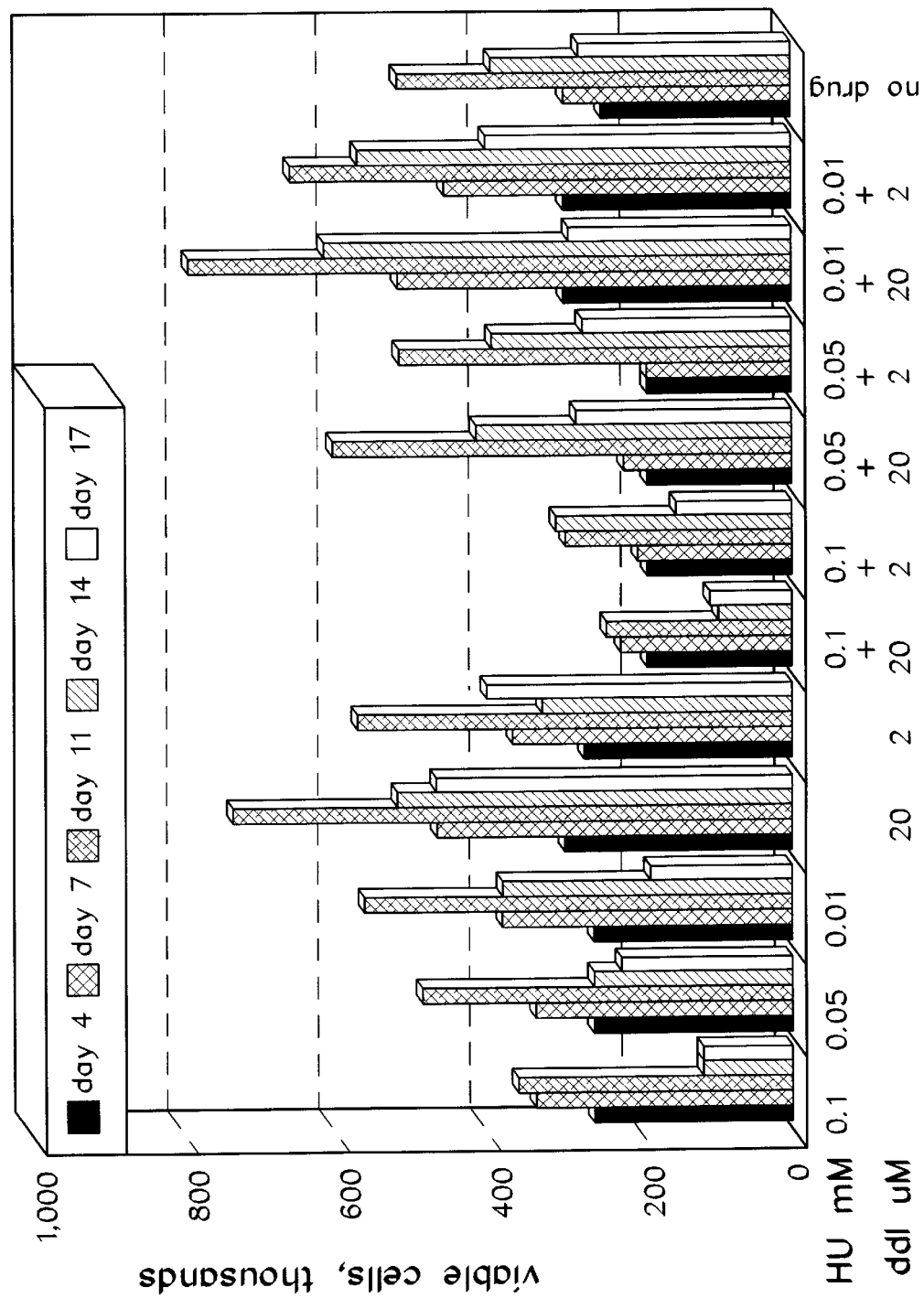
FIG. 1b graphically depicts the number of viable PBL in an HIV-1 infected culture as a function of the hydroxyurea and ddI concentrations.

The present invention is based on the discovery that a reduction of the intracellular deoxynucleoside triphosphate (dNTP) concentration selectively inhibits the replication of reverse transcriptase dependent viruses. An approach to virus inhibition that is based on this strategy advantageously avoids triggering the formation of viral escape mutants. Conversely, direct selective pressure against viral proteins would be expected to promote the formation of such mutants.

In the practice of the present invention, hydroxyurea is one preferred compound that depletes intracellular dNTP levels. This compound is one of many inhibitors of ribonucleotide reductase, an enzyme catalyzing the reduction of ribonucleoside diphosphates to their deoxyribonucleoside counterparts for DNA synthesis. Other ribonucleotide reductase inhibitors include guanazole, 3,4-dihydroxybenzohydroxamic acid, N,3,4,5-tetrahydroxybenzimidamide HCl, 3,4-dihydroxybenzamidoxime HCl, 5-hydroxy-2-formylpyridine thiosemicarbazones, and α-(N)-heterocyclic carboxaldehyde thiosemicarbazones, 4-methyl-5-amino-1-formylisoquinoline thiosemicarbazone, N-hydroxy-N'-amino-guanidine (HAG) derivatives, 5-methyl-4-aminoisoquinoline thiosemicarbazone, diaziquone, doxorubicin, 2,3-dihydroxylbenzoyl-dipeptides and 3,4-dihydroxylbenzoyl-dipeptides, iron-complexed 2-acetylpyridine 5-[(2-chloroanilino)-thiocarbonyl]-thiocarbonohydrazone (348U87), iron-complexed 2-acetylpyridine-5-[(dimethylamino)thiocarbonyl]-thiocarbonohydrazone (A111OU), 2'-deoxy-2'-methylenecytidine 5'-diphosphate (MdCDP) and 2'-deoxy-2', 2'-difluorocytidine 5'-diphospahte(dFdCDP),2-chloro-9-(2-deoxy-2-fluoro-β-D-arabinofuranosyl)-adenosine (Cl-F-ara-A), diethyldithiocarbamate (DDC), 2,2'-bipyridyl-6-carbothioamide, phosphonylmethyl ethers of acyclic nucleoside analogs, [eg. diphosphates of N-(S)-(3-hydroxy-2-phosphonylmethoxypropyl and N-2-phosphonylmethoxyethyl) derivatives of purine and pyrimidine bases], nitrosourea compounds, acylclonucleoside hydroxamic acids (e.g., N-hydroxy-α-(2-hydroxyethoxy)-1 (2H)-pyrimidineacetamides 1–3, and 2-acetylpyridine 4-(2-morpholinoethyl)thiosemicarbazone (A723U)).

Compounds that inhibit dNTP synthesis or that otherwise deplete the intracellular pool of at least one dNTP may be administered by any conventional route. Where treated cells are in vitro, the compound may simply be introduced into the medium in which the cells are growing. On the other hand, where cells to be treated are part of a larger organism, that is, where treatment is in vivo, administration to an animal may be via the oral route, or may be intravenous, intraperitoneal, intramuscular, subcutaneous, transdermal, transmucosal (e.g., by inhalation or by means of a suppository), or by any other suitable route. Administration to plants may be accomplished by spraying, dusting, application in irrigation water, or by any other conventional means.

It should be noted that depletion of the intracellular pool of any one of the four deoxynucleoside phosphates is considered to be within the scope of the present invention. Furthermore, depletion of mono-, di-, or triphosphates of nucleosides is also within the scope of this invention.

The particular dosage, toxicity, and mechanism for delivery of the dNTP-depleting drugs of the present invention are either already known, or can be readily determined by conventional empirical techniques. Although some of the dNTP-depleting compounds may exhibit limiting toxicity or difficulties in intracellular delivery, others (such as hydroxyurea) have been extensively studied and found to have favorable pharmacological properties.

Suitable human dosages for these compounds can vary widely. However, such dosages can readily be determined by those of skill in the art. For example, dosages to adult humans of from about 0.1 mg to about 1 g or even 10 g are contemplated.

In one preferred embodiment, the dosage is such that the intracellular dNTP pool is depleted to a concentration that is below the $K_m$ of the viral reverse transcriptase, but above the $K_m$ of endogenous cellular polymerases, such as DNA polymerase $\alpha$, $\beta$, and $\gamma$. This permits selective inhibition of viral replication without significant cellular toxicity.

Hydroxyurea has been widely used in cancer therapy as a broad spectrum antineoplastic drug (R. C. Donehower, *Seminars in Oncology* 19 (Suppl. 9), 11 (1992)). Hydroxyurea is readily absorbed after oral ingestion, rapidly distributed in the body fluids, including the cerebrospinal fluid, and enters cells efficiently by passive diffusion (Id.). Its toxic effects are less profound and easier to control than other chemotherapeutic drugs (Id.).

In human chemotherapy, hydroxyurea is currently administered using two basic schedules: (a) a continuous daily oral dose of 20–40 mg per kg per day, or (b) an intermittent dose of 80 mg per kg per every third day. Either schedule could be used in the treatment of viral infections. However, because response to treatment is variable, peripheral white blood cell counts must be monitored so that treatment can be stopped when leukopenia occurs. Similar dosage ranges may be used in the practice of the present invention.

Given that viral reverse transcriptase is generally quite sensitive to decreased levels of dNTP, lower dosages of hydroxyurea may also be effective in treating viral infections. Such low dosages of hydroxyurea would reduce the toxicity to white blood cells. Any dosage that effectively decreases the replication of RT-dependent viruses would be useful in chronically treating AIDS patients.

In the practice of the present invention, the inhibition of reverse transcriptase activity and the impairment of HIV-1 DNA synthesis are accomplished by treating cells with hydroxyurea. Under the specified conditions, incomplete HIV-1 DNA was formed without apparent toxic effects to the cells. Incomplete viral DNA has been shown to be rapidly degraded in PBL (Zack, et al., supra, 1990 and 1992). Therefore, the present invention provides a new method to inhibit HIV replication by modulating intracellular dNTP pools. This is accomplished by employing drugs such as hydroxyurea at pharmacological ranges.

The present invention also encompasses antiviral therapies that are based on the use of dNTP-depleting drugs in conjunction with conventional or novel nucleoside phosphate analogs. By depleting the intracellular dNTP pool, drugs such as hydroxyurea are expected to increase the therapeutic effect of treatment of HIV infection by nucleoside phosphate analogs such as AZT, ddI, ddC, 2'-F-dd-ara-A, 2'-F-dd-ara-I and 2'-F-dd-ara-G. These analogs act as competitors of cellular dNTP according to an antiviral mechanism that is distinct from that of hydroxyurea. A description of the 2'-fluoro nucleosides has been presented by Marquez et al. in *J. Med. Chem.* 33:978–985 (1990). Currently, antiviral therapy requires doses of AZT or ddI at 500 mg per day or ddC at 2 mg per day for an adult human. Similar dosages may be used in the present invention. However, use of dNTP depleting drugs may increase the effectiveness of these nucleoside phosphate analogs so that they can be used at lower dosages or less frequently.

One of the problems in using antiviral nucleoside phosphate analogs is the appearance of escape mutants. Such variants usually derive from mutations in the gene that encodes RT. We believe the appearance of RT mutants that can function using low levels of nucleotides will be an unlikely event. Hence, we believe that antiviral drugs, such as hydroxyurea, which deplete intracellular dNTP pools will be unlikely to favor the evolution of RT escape mutants. Furthermore, drugs that deplete the intracellular dNTP pool could be of value in the treatment of viral disease in cases where RT escape mutants have appeared.

Because dNTP-depleting drugs and nucleoside phosphate analogs have different inhibitory mechanisms, we predict that combinations of these agents will result in synergistic inhibitory effects. By depleting the intracellular nucleotide pool with hydroxyurea or a similarly acting drug, the therapeutic effects of nucleoside phosphate analogs, which act as competitors of dNTP, are expected to increase. Such a combination drug treatment may also result in decreased toxicity since lower dosages of nucleoside phosphate analogs would be rendered more effective.

Because HIV-1 RT is a distributive enzyme, we expected that low levels of dNTPs induced by drugs such as hydroxyurea would affect RT more than the cellular DNA polymerases a, 6, and V, which are known to be processive enzymes (Huber, et al, supra; Kati, et al., supra; U. H übscher, supra). This selective effect on RT may result in lower cellular toxic effects than occur with other antiviral drugs.

Unlike retroviruses, HBV is a DNA virus with a partially double-stranded and partially single-stranded genome. However, like retroviruses, reverse transcription is required early in the process of HBV genome replication. The RT is specified by the HBV genome and synthesized in the infected host liver cell where viral replication occurs.

Because replication of the HBV viral genome is dependent on RT, it is expected that the method of limiting dNTP pools by treating people with therapeutic drugs that inhibit dNTP synthesis would also be effective in limiting HBV viral replication. Drugs such as hydroxyurea that diffuse into nearly all cell types would be particularly advantageous in controlling hepatic replication of HBV.

Limiting HBV replication has two important effects. First, it limits the spread of infectious virions from carriers to uninfected individuals. Second, it decreases the symptoms such as chronic hepatitis in infected individuals. Generally, liver function improves after HBV replication ceases. Also, because the incidence of HCC is much higher in HBV-infected humans, decreased infection in the population presumably would result in a decreased incidence of liver cancer.

As described above, the use of hydroxyurea (or similar dNTP-limiting drugs) in conjunction with antiviral drugs, such as adenine arabinoside, ara-monophosphate, acyclovir, 6-deoxyacyclovir, and α, β, and γ interferons, that act via other mechanisms could also increase the effectiveness of these anti-HBV drugs. This is especially predicted for adenine arabinoside which acts as a competitive inhibitor in a mechanism analogous to that of antiviral nucleoside phosphate analogs used to treat HIV infections. Furthermore, treatment with hydroxyurea (or similar dNTP-limiting drugs) could make antiviral drugs more effective at lower doses than required for treatment solely using antiviral drugs.

As described above, the method of using hydroxyurea (or similar dNTP-limiting drugs) on people whose HBV infections have become refractory to antiviral drugs is also anticipated in the present invention.

Other viruses that infect animals or plants are also dependent on RT activity for their replication. Cauliflower mosaic virus is one example of a virus that uses a RT in replication of its DNA genome.

The botanical use of compounds that limit intracellular dNTP pools to inhibit viral replication of other reverse transcriptase dependent viruses is within the scope of the present invention, as is the use of such compounds on animals, including humans, infected with a wide variety of RT-dependent viruses.

The rationale for the present invention and the practice of the present invention may be better understood by reference to the following nonlimiting examples. A key step of HIV-1 infection of PBL is the conversion of the viral RNA genome into double-stranded DNA by the action of HIV-1 RT. Viral DNA synthesis differs in different states of infected PBL. In quiescent PBL, viral DNA synthesis can be initiated as efficiently as in mitogen-stimulated PBL. However, in contrast to the stimulated cells, DNA synthesis in quiescent PBL may terminate prematurely (J. A. Zack, et al., *Cell* 61:213 (1990); J. A. Zack, et al., *Virology* 66:1717 (1992)) producing no HIV-1 progeny (Zack, et al, supra; M. Stevenson, et al., *EMBO J.* 9:1551 (1990); M. I. Bukrinsky, et al., *Science* 254:423 (1991)). This process results in a pool of unintegrated viral DNA (Stevenson, et al., supra; Bukrinsky, et al., supra), which can remain latent in both in vitro infected quiescent PBL and in vivo infected resting PBL (Zack, et al., supra, 1990 & 1991; Stevenson, et al., supra; Bukrinsky, et al., supra). Stimulation of these cells can rescue HIV-1 DNA, leading to integration and production of viral progeny (ld.). Incomplete viral DNA has also been found associated with HIV-1 mature infectious particles, but the biological role of this DNA is unclear (F. Lori, et al., *J. Virol.* 66:5067 (1992); D. Trono ibid. 66:4893 (1992)).

Example 1 illustrates a method that can be used to quantitate the replication of the HIV-1 genome in infected cells. In this example, the rates of HIV-1 DNA synthesis in infected quiescent and stimulated PBL were quantitatively analyzed using a polymerase chain reaction (PCR) assay.

EXAMPLE 1

HIV Replication

The PCR assay, previously applied to quantitate HIV-1 DNA in mature HIV-1 virions (F. Lori et al., supra; D. Trono, supra), was used to amplify several regions of the HIV-1 genome. The primer pairs used to amplify the viral DNA were M667/AA55, M667/BB301, and M667/M661 (M. Stevenson et al., supra; M. I. Bukrinsky, et al., supra). M667 is a sense primer in the R region of the long terminal repeat (LTR). AA55 is an antisense primer immediately 5' to the PB (tRNA primer binding) region. The M667/AA55 primer pair amplifies the negative strand region initially synthesized by RT to yield a product called R-U5. BB301 is complementary to the PB region. Amplification by M667/BB301 can be achieved in the presence of positive stand DNA which has been synthesized starting at the polypurine tract upstream from the right LTR and, after jumping to the other end of the template, extended up to the PB region to yield a product called R-PB (H. E. Varmus and R. Swanstrom, in *Replication of Retroviruses*, RNA Tumor Viruses. R. Weiss, N. Teich, H. Varmus, J. Coffin, Eds. (Cold Spring Harbor Laboratory, Cold Spring Harbor, 1984), pp. 369–512). The negative strand, which is not fully completed, is not expected to be amplified because the RNA sequences which are complementary to the PB region have been digested in these experiments. M661 is an antisense primer in the gag region. Amplification by M667/M661 reflects the presence of complete negative strand DNA to yield a product called R-gag. These primers were designed to estimate the extent of reverse transcription at three different replicative steps: R-U5, initial negative strand synthesis; R-PB, initial positive strand synthesis up to the tRNA primer binding region; and R-gag, complete negative strand synthesis. These steps occur in subsequent order during reverse transcription (Varmus and Swanstrom, supra). If the DNA carried by the virus was a full-length negative strand DNA, the three regions analyzed by quantitative PCR should be amplified to equivalent levels. β globin sequences were amplified from the same DNA extracts in order to normalize the amount of DNA used as described in J. A. Zack et al., supra (1990); and J. A. Zack etal., supra (1992).

Viral DNA was detected immediately after infection of quiescent PBL and the amount of DNA observed at that time was proportional to the initial multiplicity of infection (MOI) of the HIV-1 IIIB strain (M. Popovic, et al., *Science* 224:497 (1984)). MOI of 1 and 10 were used and viral DNA was detected comparable to HIV-1 DNA standards corresponding to about 100 and 1000 copies, respectively, of HXB2(RIP7) plasmid DNA (J. M. McCune, et al., *Cell* 53:55 (1988)) for the R-U5, R-PB and R-gag regions.

This DNA was incompletely replicated, the typical form associated with the mature HIV-1 particles (F. Lori etal., supra; D. Trono supra). These results suggest that a portion of the incomplete DNA observed in PBL at early phases of infection was contributed by the DNA carried by the infectious viruses. Viral DNA synthesis for 72 hours after infection was next analyzed. HIV-1 DNA synthesis in quiescent PBL was significantly slower and less efficient than in stimulated PBL. In particular, in quiescent PBL the initial synthesis of viral DNA at the origin of retroviral DNA replication (immediately upstream to the tRNA primer binding region, represented by the R-U5 product of the PCR reaction) was achieved relatively early after infection (after 10 hours), while the completion of full-length negative strand DNA synthesis was significantly delayed (between 48 and 72 hours post-infection, represented by the R-gag product of the PCR assay). In contrast, synthesis of full-length negative strand DNA was completed within 10 hours after infection in stimulated PBL. Moreover, in stimulated PBL the DNA synthesis progressively increased during the time course at much higher levels than in quiescent PBL.

In summary, we found the total amount of viral DNA produced in quiescent PBL was significantly less than that produced in stimulated PBL. Even at 72 hours, the amount of viral DNA in quiescent PLB was about 10-fold less than the amount produced in stimulated PBL after 10 hours of growth. After 72 hours of growth, the total amount of viral DNA produced in stimulated PBL was at least 100-fold more than the amount produced in quiescent PBL.

Conflicting observations have been reported previously regarding the form of HIV-1 DNA in infected quiescent lymphocytes. An incomplete DNA in infected quiescent cells was reported by Zack et al. (supra, 1990 and 1992). On the other hand, Stevenson etal. (supra) showed latent complete DNA was present in quiescent PBL, but this DNA was unintegrated. These discrepancies could be explained by our findings that DNA synthesis proceeds in a slow and inefficient manner in quiescent PBL.

Previous studies have shown that cellular enzymes which are responsible for dNTP synthesis, such as thymidine kinase and deoxycytidine kinase, have extremely low activities in quiescent PBL, that increase dramatically in activated PBL (L. Pegoraro and M. G. Bernengo, *Exp. Cell Res.* 68:283 (1971)). Low levels of dNTP synthesis and the high turnover rate of dNTP during DNA replication (J. Ji and C. K. Mathews, *Mol. Gen. Genet.* 226:257 (1991)) would deplete the intracellular dNTP pool. In steady-state kinetics, if the dNTP pools were significantly lower than the Michaelis constant, $K_m$, most of the catalytic potential of HIV-1 RT would be wasted and the rate of the viral DNA synthesis would be expected to be very sensitive to changes in dNTP concentrations (I. H. Segel, in *Biochemical Calculations* (John Wiley & Sons, New York, 1975)).

Example 2 illustrates the correlation between the low levels of dNTP in quiescent PBL and the low rate of viral DNA synthesis that was described above.

EXAMPLE 2

Correlation Between dNTP Pool and HIV Replication

PBLs were cultured in the presence or absence of phytohemagglutinin A (PHA) at 10 pg/ml for 48 hours. Intracellular dNTP were extracted with 60% methanol and were examined by an enzyme assay using synthetic oligonucleotides (P. A. Sherman and A. J. Fyfe, *Anal. Biochem.* 180:222 (1989)). Data represent the mean value of three experiments. Km values were determined using a 600-base globin mRNA as template and were 3.8, 4.0, 3.9, and 2.6 $\mu$M for dCTP, dTTP, dGTP, and dATP, respectively. The cellular volume of PBL was measured using a Coulter counter chanalizer and found to be approximately 0.25 $\mu l/10^6$ cells for quiescent PBL and 0.38 $\mu l/10^6$ cells for stimulated PBL, respectively.

As shown in Table 1, the levels of dNTP in quiescent PBL were significantly lower than in the stimulated PBL. The latter were significantly higher than the $K_m$ of HIV-1 RT. Similar results were obtained after infection with HIV-1.

TABLE 1

Comparison of deoxyribonucleoside triphosphate pools ($\mu$M) in quiescent and PHA stimulated PBL cells.

| Treatment | dATP | dGTP | dCTP | dTTP |
|---|---|---|---|---|
| PBL | 0.32 ± 0.04 | 0.52 ± 0.12 | 1.48 ± 0.40 | 5.60 ± 0.80 |
| PBL + PHA | 3.24 ± 0.08 | 8.00 ± 2.67 | 18.13 ± 1.86 | 26.13 ± 1.60 |

We also assessed the in vitro activity of recombinant HIV-1 RT at dNTP concentrations that were equivalent to those found in quiescent and stimulated PBL. DNA was synthesized using a globin mRNA template and an oligo $dT_{16}$ primer (a primer extension assay). The HIV-1 RT reaction mixture contained 50 mM Tris-HCI (pH 8.0), 6 mM $MgCl_2$, 76 mM KCI, 0.5 mM DTT, 80 nM globin mRNA primed with oligo $dT_{16}$ in 1:5 ratio, and dNTP at (a) the concentrations equivalent to quiescent cells and (b) the concentrations equivalent to stimulated cells as described in Table 1. Recombinant HIV-1 RT (obtained from American Biotechnologies) was used at 5 U/ml.

Under the nucleotide concentrations that characterized quiescent conditions, the rate and yield of total DNA synthesis were profoundly lower than those corresponding to the stimulated condition. The rates of dTMP incorporation by HIV-1 RT for quiescent conditions and stimulated conditions are presented in Table 2. This could explain why DNA synthesis was slower and less efficient in quiescent than in stimulated PBL.

TABLE 2

Rates of dTMP incorporation in vitro (pmol per unit of HIV-1 RT) in quiescent (−PHA) and stimulated (+PHA) PBL

| PBL | Incubation Time (min) | | | | |
|---|---|---|---|---|---|
| | 0 | 30 | 60 | 90 | 120 |
| −PHA | 0 | 1.2 ± 0.1 | 4.2 ± 0.8 | 7.6 ± 0.8 | 12.8 ± 1.6 |
| +PHA | 0 | 21.6 ± 2.2 | 49.6 ± 5.8 | 104.4 ± 13.6 | 153.0 ± 10.6 |
| ratio of +PHA/ −PHA | | 18.0 | 11.8 | 13.7 | 12.0 |

The mode of action of HIV-1 RT and the size of the DNA products were further examined using the primer extension assay described above except that the template-primer was a 600-base globin mRNA primed with oligo($dT)_{16}$ that was $^{32}$[P]-labeled at the 5' end. Aliquots were harvested at 0, 15, 30, 60, and 120 minutes. Reaction products were separated by (a) 15% and (b) 6% polyacrylamide gel electrophoresis.

Two types of HIV RT activities were evident: an initial distributive activity and a later processive activity. In the initial distributive phase, the RT often became dissociated after incorporation of a dNTP into the nascent chain, giving rise to discrete molecular weight DNA products. This was particularly evident at dNTP concentrations characteristic of quiescent PBL. In the gel lanes, this gave rise to the ladder appearance of products ranging in size from the 16-mer primer (at time 0) to approximately a 70-mer (after 60 minutes under quiescent conditions). After 120 minutes incubation at quiescent PBL conditions, the longest DNA products measured approximately 70–100 nt. After approximately 70 new nucleosides (nt) were added, the processivity of HIV-1 RT increased and higher molecular weight DNA was synthesized. Processivity was observed primarily at dNTP concentrations similar to those in stimulated PBL. Processivity was seen after 15 minutes incubation under stimulated PBL conditions resulting in DNA products over 70–100 nt; and it continued throughout the experiment resulting in full-length transcripts after 120 minutes incubation. In contrast, little or no processivity was seen under quiescent PBL conditions, even after 120 minutes of incubation. These results suggest that low concentrations of endogenous dNTP alone are sufficient to explain the impaired DNA elongation observed in quiescent PBL.

This biphasic pattern of HIV-1 RT activity is in agreement with the enzyme kinetics studies from others (H. E. Huber etal., *J. Bio. Chem.* 264:4669 (1989); W. M. Kati, K. A.

Johnson, L. F. Jirva, K. S. Anderson, ibid. 267:25988 (1992)) and differs from the action of most of the replicative DNA polymerases which are processive polymerases, such as E. coli pol I and III, HSV DNA polymerase, and mammalian DNA polymerases α and γ (Huber, et al, supra; Kati, et al, supra; U. Hübscher, Experientia 39:1 (1983)).

Example 3 illustrates both that hydroxyurea can be used to deplete the intracellular dNTP concentration, and that such suboptimal concentrations of dNTP cause incomplete HIV-1 DNA synthesis in PBL. The 1 mM hydroxyurea concentration used in these procedures approximates the blood concentration of this drug during standard clinical protocols in humans (R. C. Donehower, Seminars in Oncology 19 (Suppl. 9), 11 (1992)). Notably, hydroxyurea did not directly inhibit RT enzymatic activity even at a 200-fold higher concentration (200 mM).

EXAMPLE 3

Use of Hydroxyurea to Inhibit HIV Replication

HIV-1 DNA synthesis was measured after infection of mitogen (PHA) stimulated PBL in the presence or absence of hydroxyurea. After 48 hours of PHA stimulation and 24 hours pretreatment with 1 mM hydroxyurea, cells were infected with HIV-1 IIIB (Popovic et al., supra) in the presence of hydroxyurea. Control cells were treated similarly, but hydroxyurea treatment was omitted. Cell aliquots were harvested 24, 48 and 72 hours after infection and analyzed for the rate of dNTP synthesis inhibition (Sherman and Fyfe, supra) measured as the percentage of dNTP levels compared to the control cells.

The results of this study, illustrated in Table 3, show that dNTP pools were substantially depleted in stimulated PBL incubated in the presence of 1 mM hydroxyurea.

TABLE 3

Effect of hydroxyurea on dNTP pools in treated PBL relative to untreated control PBL (% of untreated control amount).

| | Incubation Time (hours) | | | |
|---|---|---|---|---|
| dNTP | 0 | 24 | 48 | 72 |
| dATP | 100 ± 10 | 19 ± 2 | 19 ± 1 | 7 ± 0.5 |
| dGTP | 100 ± 10 | 70 ± 5 | 45 ± 3 | 32 ± 3 |
| dCTP | 100 ± 10 | 82 ± 9 | 61 ± 6 | 35 ± 4 |
| dTTP | 100 ± 10 | 115 ± 10 | 34 ± 2 | 23 ± 3 |

In addition, HIV-1 DNA synthesis was measured after infection of PHA-stimulated PBL in the presence or absence of hydroxyurea using the PCR analysis as described above. Standards used for comparison were serial dilutions of HXB2(RIP7) plasmid DNA (number of copies; McCune et al., supra) and β globin DNA (nanograms).

Depletion of dNTP significantly affected the HIV-1 DNA synthesis rate and inhibited the completion of viral DNA synthesis in stimulated PBL. Furthermore, dNTP depletion delayed production of full-length negative strand viral DNA which was seen in only limited amounts (approximately 10-fold to 100-fold less over a 72 hour period) relative to cells that were not treated with hydroxyurea. The pattern of inhibition was quite similar to that observed in quiescent PBL. After 72 hours, cell viability was comparable between hydroxyurea treated and untreated cells.

Because most circulating lymphocytes in vivo are quiescent, the relevance of the population of quiescent infected PBL serving as a reservoir of inducible HIV-1 has been recognized (Zack, et al., supra, 1990 and 1992; Stevenson, et al., supra; Bukrinsky, et al., supra). The latent viral DNA pool in these cells clearly plays a role in viral rescue after mitogenic stimulation (Id.). Our results suggest a mechanism of inefficient reverse transcription and subsequent formation of latent HIV-1 DNA in quiescent PBL. Although other mechanisms may also block HIV-1 replication in quiescent PBL, naturally occurring low levels of dNTP are sufficient to inhibit reverse transcription.

Example 4 illustrates that treatment of target cells with hydroxyurea, alone or in combination with the nucleoside phosphate analog ddI, inhibits HIV-1 viral expression. In particular, viral expression of RT in HIV-1 infected PHA-stimulated PBL was significantly reduced by pre-infection treatment with 1 mM hydroxyurea.

EXAMPLE 4

Use of Hydroxyurea and/or ddI to Inhibit HIV Expression

PBL were stimulated with PHA for 48 hours and treated with 1 mM hydroxyurea for 24 hours prior to infection with HIV-1 IIIB (Popovic, et al., supra) in the presence of the drug. Control cells were treated similarly except that hydroxyurea treatment was omitted. Cell supernatant aliquots were harvested two, five and nine days after infection and assayed for RT activity. RT activity was monitored as in Example 2. The results of this procedure are presented in Table 4.

TABLE 4

Inhibition of HIV-1 RT expression in infected PBL treated with 1 mM hydroxyurea (HU)

| | RT Activity (cpm/ml × 1000) at Days | | |
|---|---|---|---|
| Treatment | 2 | 5 | 9 |
| +HU | 0.892 | 0.589 | 0.434 |
| −HU control | 0.863 | 3.951 | 81.263 |

When PBL cells were treated with a combination of hydroxyurea and ddI, HIV protein p24 expression detected in cell supernatants significantly decreased (Table 5).

TABLE 5

Viral expression of p24 protein after HIV-1 infection of PHA-stimulated PBL in the presence of μM of hydroxyurea (HU) and/or ddI (ddI).

| | p24 (ng/ml) after infection (days) | | |
|---|---|---|---|
| Treatment | 4 | 8 | 12 |
| none (control) | 5 | 142 | 195 |
| ddI | | | |
| 0.2 | 4 | 116 | 197 |
| 1 | 3 | 90 | 196 |
| 5 | 1 | 58 | 125 |
| 20 | 1 | 25 | 51 |
| HU | | | |
| 10 | 4 | 100 | 204 |
| 50 | 3 | 113 | 148 |
| 100 | 2 | 111 | 116 |
| HU + ddI | | | |
| 10 + 0.2 | 3 | 144 | 200 |
| 10 + 1 | 2 | 95 | 158 |

TABLE 5-continued

Viral expression of p24 protein after HIV-1 infection of
PHA-stimulated PBL in the presence of μM of
hydroxyurea (HU) and/or ddI (ddI).

| Treatment | p24 (ng/ml) after infection (days) | | |
|---|---|---|---|
| | 4 | 8 | 12 |
| 10 + 5 | 2 | 74 | 127 |
| 10 + 20 | 0 | 19 | 44 |
| 50 + 0.2 | 2 | 109 | 146 |
| 50 + 1 | 1 | 70 | 128 |
| 50 + 5 | 0 | 12 | 24 |
| 50 + 20 | 0 | 0 | 0 |
| 100 + 0.2 | 2 | 105 | 95 |
| 100 + 1 | 0 | 55 | 71 |
| 100 + 5 | 0 | 2 | 4 |
| 100 + 20 | 0 | 0 | 0 |

Furthermore, the hydroxyurea and ddI synergistically inhibited HIV-1 p24 expression. That is, p24 expression decreased more when cells were treated with both drugs rather than one or the other drug alone. For example, Table 5 shows that treatment of cells with 5 μM ddI yielded 125 ng of p24 per ml of cell supernatant after 12 days of infection, while treatment with 50 μM hydroxyurea yielded 148 ng/ml after 12 days of infection. However, when cells were treated with both 5 μM ddI and 50 μM hydroxyurea, only 24 ng/ml of p24 were detected at day 12 after infection. Because of this synergistic effect, lower concentrations of hydroxyurea and ddI in combination could effectively eliminate p24 expression compared to treatment with only hydroxyurea or ddI at the same concentrations.

Whereas the procedure in Example 4 involved the pretreatment of target cells with hydroxyurea and/or ddI before infection, we also investigated the effect of drug treatment in cells that were already infected with the HIV-1 IIIB virus. In the latter procedure, we measured p24 production during the course of an in vitro infection to assess the inhibition of HIV-1 replication in activated PBL.

Example 5 illustrates how hydroxyurea, either alone or in combination with ddI effects the production of p24 in HIV-1 IIIB infected cells.

EXAMPLE 5

Effect of Hydroxyurea on p24 Production

PBL from healthy donors were infected for 2 hour at 37° C. with HIV-1[HTLV-IIIB] (m.o.i.=1) after 2 days stimulation with PHA and Interleukin-2 (IL-2). After washing out the residual virus, cells were treated with hydroxyurea and/or ddI at the concentrations indicated (supernatant with no drug was used as control). Every 3–4 days, supernatant was harvested for p24 analysis, cells were counted and fresh supernatant and drugs were added. Samples were analyzed for (a) p24 production in the supernatant, (b) count of viable cells, and (c) ratios between the values expressed in (a) and (b). The results from this procedure are presented in FIGS. 1a–1c.

As shown in FIG. 1a, when used alone at low concentrations, or in combination with ddI, HIV-1 replication was inhibited in a dose-dependent manner. Notably, the combination of hydroxyurea and ddI completely blocked HIV-1 replication (>99.9%), thus illustrating the powerful synergistic effect of this drug combination. Cell toxicity analysis reflected the known properties of the two drugs.

Hydroxyurea is known to act mainly as a cytostatic drug. However, continuous drug exposure eventually results in some cytotoxic effects (Yarbro, J. W., Semin. Oncol. 19:1 (1992)). This was also observed in our experiments at 0.1 mM hydroxyurea concentrations (FIG. 1b). However, both cytostatic and cytotoxic effects virtually disappeared when the drug concentration was decreased (FIG. 1b). Cytotoxicity of ddI is known to be low at the doses used in our experiments, which correspond to the plasma concentrations observed in AIDS treated patients (Faulds, D. and Brogden, R. N. Drugs 44:94 (1992)). The combination of the two drugs did not significantly change the cytotoxicity compared to the use of hydroxyurea alone. This represents a further advantage of the hydroxyurea/ddI combination since the antiviral effects were synergistically augmented without a significant increase in cytotoxicity.

To understand whether the different number of viable cells observed at different drug concentrations or during the course of infection could have affected our data (less cells alive yielding less virus production), we normalized the p24 expression to the number of viable cells (FIG. 1c). Our results showed the antiviral effect of hydroxyurea at low concentrations is not mediated by cytotoxicity.

We also investigated the inhibitory effects of hydroxyurea, either alone or in combination with AZT, on HIV-1 infection of primary human macrophages. Although we found greater variability among different experiments that employed macrophages compared to our results with primary PBL (note that in each experiment the same donor was used as a source of both PBL and macrophages), the dose-dependent inhibition of HIV-1 production by hydroxyurea was nonetheless consistently more potent than with primary PBL.

Example 6 illustrates the effectiveness of hydroxyurea as an inhibitor of HIV infection in macrophages. Moreover, this example illustrates the powerful synergistic effect of hydroxyurea and AZT as inhibitors of HIV infection of macrophages.

EXAMPLE 6

Time Course of HIV-1 Inhibition by Hydroxyurea and/or AZT in Macrophages

Figure 2:
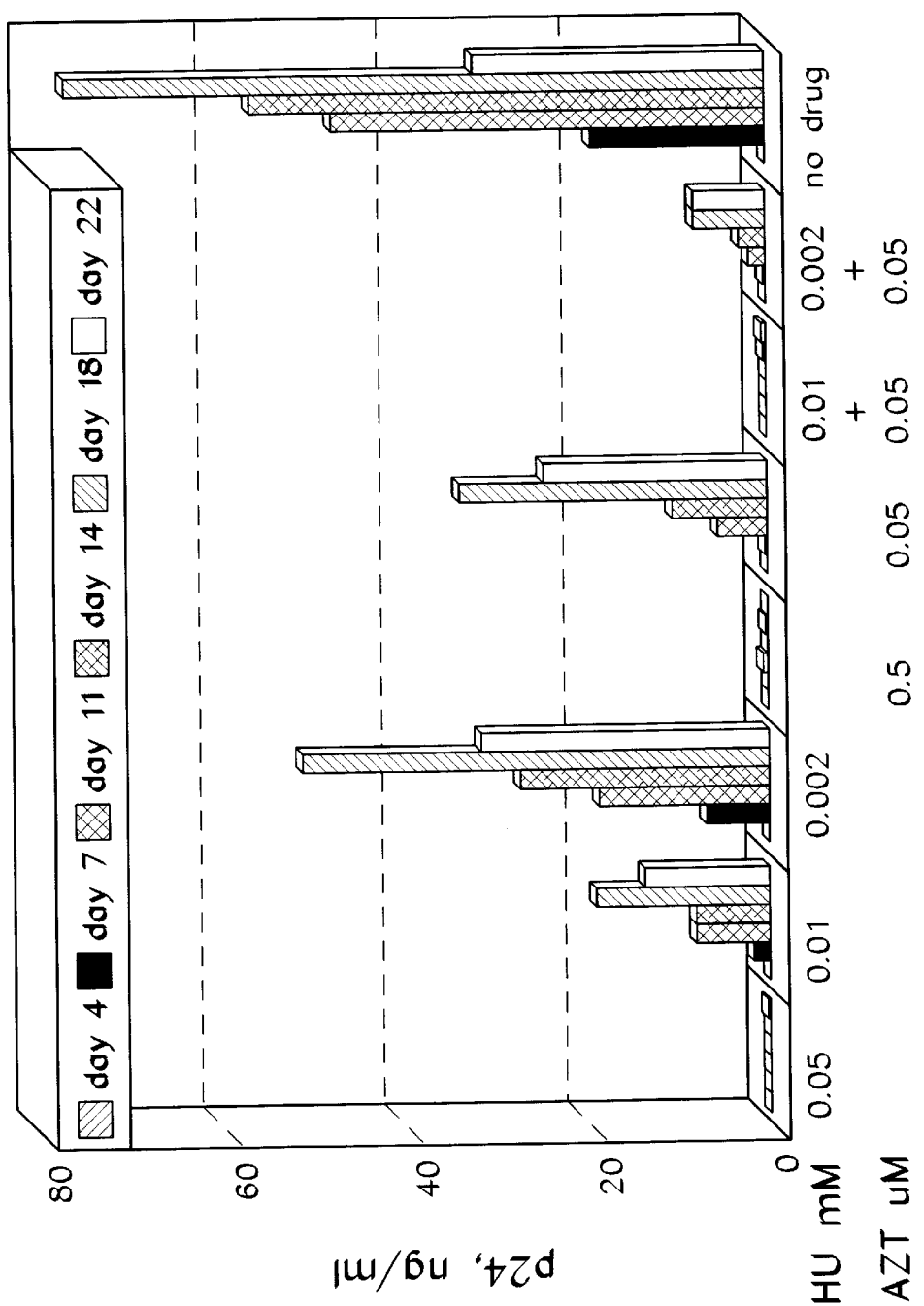
FIG. 2 graphically depicts p24 expression in HIV-1 infected human primary macrophages as a function of hydroxyurea and AZT concentrations.

Macrophages were obtained by cell adhesion after purification of PBL from healthy donors. After 14 days treatment with granulocyte-macrophage-colony-stimulating factor, cells were infected overnight with the HIV-1 strain Ba-L (Gartner et al., Science 233:215 (1986)). Cells were subsequently washed and treated with hydroxyurea and/or with AZT at the indicated concentrations. Supernatants were harvested ever 4–5 days for p24 analysis and fresh supernatant and drugs were added. We noted that no cytotoxic effects were observed in this experiment (also see Table 6). The results of these experiments are presented in FIG. 2.

Our results show that concentrations of hydroxyurea as low as 0.05 mM blocked HIV-1 replication (>99.9%). Use of lower doses of hydroxyurea and AZT, at concentrations at which each of the two drugs were only partial effective, resulted in complete inhibition (>99.9%). The synergistic effects of hydroxyurea and AZT that were observed in macrophages were therefore consistent with the results obtained using primary PBL treated with hydroxyurea and ddI.

Our demonstration that hydroxyurea inhibited two different HIV-1 strains in primary human cells suggested this drug, either alone or in combination, could also be effective in vivo. To further test this possibility we confirmed the previous observations by employing another in vitro system for drug testing. This in vitro system made use of primary cells isolated from HIV-1-infected individuals. We believe this model of HIV-1 inhibition closely approximates in vivo conditions, since it combines the use of primary cells and viral isolates, in the setting of an infection that was established in vivo.

Example 7 illustrates that hydroxyurea, either alone or in combination with nucleoside analogs, inhibits HIV-1 replication in cells isolated directly from an HIV-1 infected patient.

Example 8 illustrates the effect of high doses of hydroxyurea on HIV-1 infection of activated PBL and macrophages that were isolated from healthy donors.

EXAMPLE 8

The Effect of High Concentrations of Hydroxyurea on HIV-1 Infection

Experiments were conducted as described in FIGS. 1 (for PBL) and 2 (macrophages) with 1 mM hydroxyurea. Percentages of HIV-1 inhibition were calculated based on p24 production compared to the untreated control. Drug treatment of macrophages was suspended after 14 days. The results of this experiment are presented in Table 6.

TABLE 6

| | | 1 mM Hydroxyurea | | | | drug suspension | | | no drug | | | | | | |
|---|---|---|---|---|---|---|---|---|---|---|---|---|---|---|---|
| | | Days after infection | | | | | | | | | | | | | |
| | | 4 | 7 | 10 | 14 | 21 | 28 | 35 | 4 | 7 | 10 | 14 | 21 | 28 | 35 |
| PBMC | HIV-1 inhibition, % | 100 | 100 | 100 | 100 | n.d. | n.d. | n.d. | 0 | 0 | 0 | 0 | n.d | n.d | n.d |
| | Viable cells, thousands/ml | 500 | 185 | 87 | 36 | n.d. | n.d. | n.d. | 500 | 610 | 1500 | 1300 | n.d | n.d | n.d |
| Macrophages | HIV-1 inhibition, % | 100 | 100 | 100 | 100 | 100 | 100 | 100 | 0 | 0 | 0 | 0 | 0 | 0 | 0 |
| | Viable cells, thousands/cm$^2$ | 300 | 280 | 270 | 270 | 260 | 240 | 190 | 300 | 310 | 310 | 290 | 270 | 230 | 200 |

PBMC = peripheral blood mononuclear cells
n.d. = not done

EXAMPLE 7

Inhibition of HIV-1 in Activated PBL from an HIV-1 Infected Patient

PBL were isolated and stimulated for 2 days with PHA and IL-2. Subsequently, hydroxyurea and ddI were added at the specified concentrations. The extent of HIV-1 infection was analyzed as described in Example 5. Samples were tested for (a) p24 production in the supernatant, (b) viable cell count.

Figure 3A:
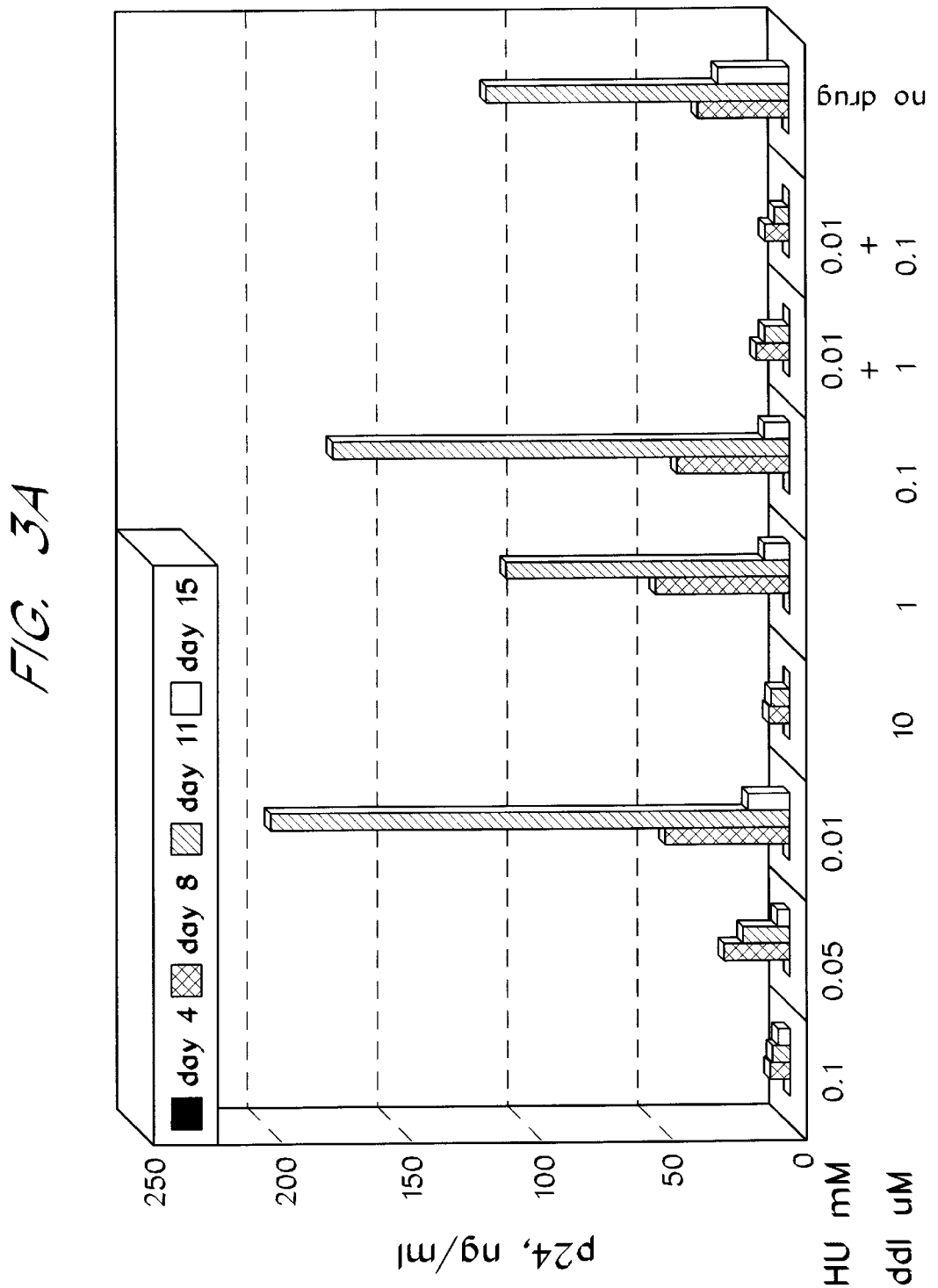
FIG. 3a graphically depicts a time course of p24 inhibition by hydroxyurea and/or by ddI in activated PBL isolated from an HIV-1 infected patient.

Once again, hydroxyurea inhibited HIV-1 replication in a dose-dependent manner and, in combination with ddI, showed strong synergistic effects (FIG. 3a). However, in some instances, both the pharmacologic and the cytotoxic effects of hydroxyurea were more pronounced (FIGS. 3a, 3b), and lower doses of hydroxyurea (compared to the experiments on PBL derived from healthy donors and illustrated in FIG. 1 were used, especially with cells from HIV-1-infected patients in the advanced stages of AIDS. Also note that at the lowest levels both hydroxyurea and ddI in some cases (as illustrated in FIG. 3) stimulated HIV-1 replication, but only when used individually.

This phenomenon was not confined to the use of cells from infected patients, since it was also occasionally observed when cells from a healthy donor were used.

Independent of the viral or cellular source, however, stimulatory effects were not observed when hydroxyurea and either of the nucleoside analogs were used in combination (not shown).

Continuous treatment with 1 mM hydroxyurea completely blocked HIV-1 replication both in activated PBL and macrophages. In activated PBL, however, toxic effects at these concentrations were observed early, in contrast with the lack of significant toxicity in macrophages. Furthermore, in some experiments the absence of HIV-1 replication in infected macrophages was documented even several weeks after discontinuing the drug treatment.

Our finding that hydroxyurea, alone or in combination with nucleoside analogs, efficiently inhibited HIV-1 replication in primary human cells in vitro suggests this drug will also be useful in human therapy.

Example 9 describes the use of hydroxyurea in a protocol designed to control in vivo HIV-1 replication, thereby benefitting the treated individual.

EXAMPLE 9

Administration of Hydroxyurea to HIV Infected Humans

One or more HIV-1 seropositive volunteers are first identified. Blood samples drawn from the volunteers are assayed for CD4$^+$T-cells using any suitable quantitation means. Such quantitation means include, but are not limited to, the flow cytometer. Over a period of from several weeks to months, the number of CD4$^+$T-cells is observed to decrease steadily as an indicator of disease progression.

The HIV-1 infected volunteers are then put on a regimen of drug therapy that includes hydroxyurea, either alone or in combination with nucleoside analogs. The nucleoside analogs can be any of ddI, ddC or AZT, or combinations thereof.

Hydroxyurea is combined with a pharmaceutically acceptable excipient and is administered in dosages of from 20–40 mg per kg per day. The drug dosage is adjusted to result in a stable hydroxyurea blood concentration of approximately 1 mM. This concentration is chosen because it approximates the blood concentration of hydroxyurea during standard clinical protocols in humans. When hydroxyurea is used in conjunction with a nucleoside analog, the dosage of the analog is determined according to convention in the medical and pharmaceutical arts.

After one month of drug treatment blood samples are again drawn and assayed for $CD4^+$T-cells. The T-cell population has stabilized or increased as an indication of the therapeutic effectiveness of the antiviral activity of hydroxyurea. The most dramatic improvements are observed in volunteers who received the combination of hydroxyurea together with a nucleoside analog.

The preceding Examples have presented results obtained using combinations of hydroxyurea and certain chain-terminating compounds, such as nucleoside analogs, to inhibit reverse transcriptase dependent viral replication. We also expect the chain-terminating efficiency of other dideoxynucleoside phosphate analogs, and derivatives thereof, to be enhanced by combination drug therapy involving hydroxyurea. Hence, fluorinated derivatives of purine dideoxynucleosides, such as those described by Marquez et al. in *J. Med. Chem.* 33:978–985 (1990), are expected to exhibit particularly potent antiviral activities when administered in combination with hydroxyurea. These fluorinated derivatives include 2'-F-dd-ara-A, 2'-F-dd-ara-l and 2'-F-dd-ara-G. Advantageously, such fluorinated derivatives are expected to be useful as oral medications because of their chemical stability under acidic conditions.

Example 9 describes an experiment that can be used to assess the in vitro anti-viral effects of hydroxyurea and various fluorinated derivatives of chain terminating nucleoside analogs.

EXAMPLE 9

Use of Hydroxyurea and Fluorinated Derivatives of Chain Terminating Nucleoside Analogs to Inhibit HIV Expression PBL isolated from healthy donors are stimulated with PHA and IL-2 for 48 hours using standard protocols. At the same time, the cells are pre-treated with hydroxyurea alone or in combination with either ddI or fluorinated derivatives of chain-terminating nucleosides. The use of ddI in this procedure serves as a positive control for hydroxyurea-enhanced inhibition of p24 production. At the end of the 48 hour period, samples of the treated cells are infected with HIV-1 IIIB (Popovic et al., supra). Aliquots of the cell supernatants are then harvested at various time points post-infection and analyzed for the presence of p24 antigen as an indicator of HIV-1 infection. Example results expected in this procedure are qualitatively presented in Table 7.

TABLE 7

Viral expression of p24 protein after HIV-1 infection of PHA-stimulated PBL in the presence of $\mu$M of hydroxyurea (HU) and/or nucleoside analogs

| Treatment | p24 Expression after Infection (Days) | | |
|---|---|---|---|
| | 4 | 8 | 12 |
| Untreated | Low | High | Very High |
| HU/50 | Low | Medium | High |
| ddI/20 | Low | Medium | Medium |
| 2'-F-dd-ara-A/20 | Low | Medium | Medium |
| 2'-F-dd-ara-I/20 | Low | Medium | Medium |
| 2'-F-dd-ara-G/20 | Low | Medium | Medium |
| HU + ddI / 50 + 20 | Low | Low | Low |
| HU + 2'-F-dd-ara-A / 50 + 20 | Low | Low | Low |
| HU + 2'-F-dd-ara-I / 50 + 20 | Low | Low | Low |
| HU + 2'-F-dd-ara-G / 50 + 20 | Low | Low | Low |

Results such as those presented in Table 7 will confirm that the antiviral activities of fluorinated chain-terminating nucleoside analogs are enhanced when used in combination with hydroxyurea.

We have demonstrated that hydroxyurea is an effective HIV-1 inhibitor. Significantly, these antiviral properties were not solely mediated by the cytostatic or cytotoxic effects of the drug in non-stimulated PBL and macrophages. We believe this was true because these cells were either quiescent (PBL) or terminally differentiated (macrophages), and therefore did not require high levels of dNTP synthesis. Even after PBL activation, when dNTP synthesis was required for cell cycling, the antiviral and cytotoxic effects could be distinguished at low drug concentrations. The selective anti-HIV-1 activity of hydroxyurea in activated PBL may be partly explained by the distributive properties of HIV-1 RT. Compared to cellular polymerases, the distributive property of RT may render it more sensitive to low intracellular concentrations of dNTP. In activated PBL, the cytostatic properties of hydroxyurea probably contributed to its antiviral activity, since viral replication in lymphocytes requires cell division.

By decreasing the intracellular concentration of dNTP while increasing the uptake and metabolism of nucleoside analogs, such as ddI or AZT, hydroxyurea decreased the ratio between intracellular dNTP and nucleoside analogs, thus enhancing their antiviral effects.

Combinations of hydroxyurea and either ddI or AZT proved to be extremely effective antiviral treatments. In particular, this combination decreased the drug concentrations necessary to obtain >99.9% inhibition of HIV-1 replication, and gave clear synergistic effects over the use of the individual drugs without increasing their cytotoxicities. The phenomenon of viral stimulation that is sometimes observed when low doses of drugs are used individually was also eliminated. The combined use of these drugs may therefore be beneficial and safe for asymptomatic, seropositive individuals.

The use of hydroxyurea in the treatment of AIDS offers several advantages.

After more than 30 years in human use, the properties of this drug are well established. As a result of its extreme diffusiblity, this drug can enter all tissues, including cells of the central nervous system, with a $V_{max}$ that appears infinite (Morgan, J. S., Creasey, D. C. and Wright, J. A., *Biochem. Biophys. Res. Commun.* 134:1254 (1986)). In view of the fact that hydroxyurea is highly effective at inhibiting HIV-1 replication in macrophages, we expect this drug to be effective against the neurological manifestations of AIDS, which are believed due to the effects of viral replication in macrophages (Koenig, S., et al., *Science* 233:1089 (1986)). The activity of hydroxyurea does not depend on the metabolism of the drug within cells. Thus, in contrast with nucleoside analogs, hydroxyurea is expected to be effective in all cells, independent of their activation state. Hydroxyurea is classified as a mildly toxic drug and does not cause immunodepression. Myelotoxicity is hydroxyurea's dose-limiting toxicity. However, such toxicity can be easily monitored and it is constantly and rapidly reversible after decreasing the dose or suspending the treatment (Donehower, R. C., *Semin. Oncol.* 19:11 (1992)). By monitoring simple parameters like peripheral cell counts, hydroxyurea can be administered for years, and sometimes decades. Furthermore, bone marrow toxicity is severe only when hydroxyurea is used at very high doses, such as those used in leukemia treatment (approximately 0.5–2.5 mM) (Belt, R. J. et al., *Cancer* 46:455 (1980)). In most of our experiments, hydroxyurea concentrations that were 2–3 logs lower than these levels still were adequate to completely inhibited HIV-1 replication. Hydroxyurea can be orally administered and is much less expensive than other drugs that are presently used for AIDS therapy. Hydroxyurea does not inhibit HIV-1 directly, but via the inhibition of the cellular enzyme ribonucleotide reductase. Cellular enzymes do not mutate under physiological conditions and one could expect that HIV-1 resistance to hydroxyurea would be far less likely to occur than with conventional drugs. This could circumvent the onset of HIV-1 escape mutants. To date, none of the anti-HIV-1 drugs that have been tested have prevented the evolution of escape mutants. This failure represents a major frustration in the battle against AIDS. Moreover, the onset of escape mutants that arise during treatment of AIDS victims with nucleoside analogs, should also be reduced when these drugs are used in combination with hydroxyurea. Since the synergistic effect of the combination of a nucleoside analog and hydroxyurea inhibits virus replication, which may be a requisite step in the process of virus mutation that leads to the development of escape mutants.

In our opinion, two main strategies utilizing hydroxyurea as AIDS therapies may be followed. The first is the use of low doses of hydroxyurea. Drug combinations are recommended in this case, for the reasons above illustrated, and trials could safety include asymptomatic seropositive individuals. The second strategy would use high levels of hydroxyurea, with protocols similar to those used in leukemia. This strategy would be more potent against HIV-1 and would also kill the replicating PBL producing virus. However, one could design a combination of both strategies by alternating high doses of hydroxyurea for purging purposes, followed by lower maintenance doses.

While particular embodiments of the invention have been described in detail, it will be apparent to those skilled in the art that these embodiments are exemplary rather than limiting, and the true scope of the invention is that defined by the claims that follow.

We claim:

1. A composition comprising hydroxyurea and 2', 3'-dideoxyinosine (ddI).

2. The composition of claim 1, wherein the amount of ddI is such as to provide a concentration of about 1 $\mu$M to 20 $\mu$M and the amount of hydroxyurea is such as to provide a concentration of about 0.01 mM to 0.1 mM.

3. The composition of claim 2, wherein the amount of ddI is such as to provide a concentration of about 1 $\mu$M and the amount of hydroxyurea is such as to provide a concentration of about 0.01 mM.

4. The composition of claim 2, wherein the amount of ddI is such as to provide a concentration of about 5 $\mu$M and the amount of hydroxyurea is such as to provide a concentration of about 0.01 mM.

5. The composition of claim 2, wherein the amount of ddI is such as to provide a concentration of about 20 $\mu$M and the amount of hydroxyurea is such as to provide a concentration of about 0.01 mM.

6. The composition of claim 2, wherein the amount of ddI is such as to provide a concentration of about 1 $\mu$M and the amount of hydroxyurea is such as to provide a concentration of about 0.05 mM.

7. The composition of claim 2, wherein the amount of ddI is such as to provide a concentration of about 5 $\mu$M and the amount of hydroxyurea is such as to provide a concentration of about 0.05 mM.

8. The composition of claim 2, wherein the amount of ddI is such as to provide a concentration of about 20 $\mu$M and the amount of hydroxyurea is such as to provide a concentration of about 0.05 mM.

9. The composition of claim 2, wherein the amount of ddI is such as to provide a concentration of about 1 $\mu$M and the amount of hydroxyurea is such as to provide a concentration of about 0.1 mM.

10. The composition of claim 2, wherein the amount of ddI is such as to provide a concentration of about 5 $\mu$M and the amount of hydroxyurea is such as to provide a concentration of about 0.1 mM.

11. The composition of claim 2, wherein the amount of ddI is such as to provide a concentration of about 20 $\mu$M and the amount of hydroxyurea is such as to provide a concentration of about 0.1 mM.

12. A method of inhibiting a human immunodeficiency virus in cells comprising administration to a host in need thereof a composition comprising hydroxyurea and 2', 3'-dideoxyinosine (ddI).

13. The method of claim 12, wherein the amount of ddI is such as to provide a concentration of about 1 $\mu$M to 20 $\mu$M and the amount of hydroxyurea is such as to provide a concentration of about 0.01 mM to 0.1 mM.

14. The method of claim 13, wherein the amount of ddI is such as to provide a concentration of about 1 $\mu$M and the amount of hydroxyurea is such as to provide a concentration of about 0.01 mM.

15. The method of claim 13, wherein the amount of ddI is such as to provide a concentration of about 5 $\mu$M and the amount of hydroxyurea is such as to provide a concentration of about 0.01 mM.

16. The method of claim 13, wherein the amount of ddI is such as to provide a concentration of about 20 $\mu$M and the amount of hydroxyurea is such as to provide a concentration of about 0.01 mM.

17. The method of claim 13, wherein the amount of ddI is such as to provide a concentration of about 1 $\mu$M and the amount of hydroxyurea is such as to provide a concentration of about 0.05 mM.

18. The method of claim 13, wherein the amount of ddI is such as to provide a concentration of about 5 $\mu$M and the amount of hydroxyurea is such as to provide a concentration of about 0.05 mM.

19. The method of claim 13, wherein the amount of ddI is such as to provide a concentration of about 20 $\mu$M and the amount of hydroxyurea is such as to provide a concentration of about 0.05 mM.

20. The method of claim 13, wherein the amount of ddI is such as to provide a concentration of about 1 $\mu$M and the amount of hydroxyurea is such as to provide a concentration of about 0.1 mM.

21. The method of claim 13, wherein the amount of ddI is such as to provide a concentration of about 5 $\mu$M and the amount of hydroxyurea is such as to provide a concentration of about 0.1 mM.

22. The method of claim 13, wherein the amount of ddI is such as to provide a concentration of about 20 $\mu$M and the amount of hydroxyurea is such as to provide a concentration of about 0.1 mM.

* * * * *